US008835664B2

(12) United States Patent
Jung et al.

(10) Patent No.: US 8,835,664 B2
(45) Date of Patent: Sep. 16, 2014

(54) FLUORINATED COMPOUND, A COMPOSITION COMPRISING THE SAME, AND A PRODUCTION METHOD FOR A FILM USING THE SAME

(75) Inventors: Soon-Hwa Jung, Daejeon (KR); Jin-Young Park, Daejeon (KR); Yeong-Rae Chang, Daejeon (KR); Eun-Kyoung Kim, Seoul (KR)

(73) Assignees: LG Chem, Ltd., Seoul (KR); Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 13/577,036

(22) PCT Filed: Feb. 1, 2011

(86) PCT No.: PCT/KR2011/000696
§ 371 (c)(1),
(2), (4) Date: Aug. 3, 2012

(87) PCT Pub. No.: WO2011/096701
PCT Pub. Date: Aug. 11, 2011

(65) Prior Publication Data
US 2012/0308802 A1 Dec. 6, 2012

(30) Foreign Application Priority Data
Feb. 4, 2010 (KR) .................. 10-2010-0010653

(51) Int. Cl.
C07F 7/04 (2006.01)
C07F 7/12 (2006.01)
C07F 7/16 (2006.01)
C07F 7/18 (2006.01)
C07F 7/02 (2006.01)
C07F 7/00 (2006.01)
C08L 83/04 (2006.01)
C08J 5/18 (2006.01)

(52) U.S. Cl.
CPC ............... *C07F 7/12* (2013.01); *C08J 2343/04* (2013.01); *C07F 7/1836* (2013.01); *C08L 83/04* (2013.01); *C08J 5/18* (2013.01)
USPC ........... 556/436; 556/431; 556/435; 556/437; 556/438; 556/440; 428/446; 428/447; 522/172; 522/99; 522/148; 522/71; 522/74; 522/162; 522/163; 522/164; 522/165; 427/508; 427/515; 427/517

(58) Field of Classification Search
USPC ......... 556/400, 431, 435, 465, 436, 437, 440; 428/446, 447; 522/172, 99, 148, 71, 522/74, 162, 163, 164, 165; 427/508, 515, 427/517
See application file for complete search history.

(56) References Cited

U.S. PATENT DOCUMENTS

| 4,201,808 | A | 5/1980 | Cully et al. |
| 4,985,473 | A | 1/1991 | Williams et al. |
| 5,204,441 | A | 4/1993 | Baum et al. |
| 5,240,774 | A | 8/1993 | Ogawa et al. |
| 6,025,017 | A | 2/2000 | Roth |
| 6,306,563 | B1 | 10/2001 | Xu et al. |
| 6,323,361 | B1 | 11/2001 | Wu et al. |
| 6,632,585 | B1 | 10/2003 | Nakamura |
| 6,716,534 | B2 * | 4/2004 | Moore et al. .................. 428/447 |
| 7,078,445 | B2 | 7/2006 | Xu et al. |
| 7,247,386 | B2 * | 7/2007 | Hooftman et al. ............ 428/447 |
| 7,327,925 | B2 | 2/2008 | Wang et al. |
| 7,723,452 | B2 * | 5/2010 | Hooftman et al. ............ 526/242 |
| 2002/0115820 | A1 | 8/2002 | Wang et al. |
| 2004/0006188 | A1 | 1/2004 | Kim et al. |
| 2007/0135602 | A1 | 6/2007 | Yamahiro et al. |
| 2007/0249858 | A1 | 10/2007 | Kinsho et al. |
| 2009/0025609 | A1 * | 1/2009 | Egami et al. ............ 106/287.12 |

FOREIGN PATENT DOCUMENTS

| EP | 0820980 B1 | 7/2001 |
| JP | 2002-243907 A | 8/2002 |
| JP | 2002243907 A * | 8/2002 |
| JP | 2005-132827 | 5/2005 |
| JP | 2008-050549 | 3/2008 |
| KR | 10-2003-0097532 | 12/2003 |
| KR | 2004-0087534 A | 10/2004 |
| KR | 10-2005-0033840 | 4/2005 |
| KR | 20090088240 A | 8/2009 |
| WO | WO 01/37049 A1 | 5/2001 |

OTHER PUBLICATIONS

Kim, E, et al., Low Optical Loss Perfluorinated Methacrylates for a Single-Mode Polymer Waveguide, Chem Mater, 2005, 17, pp. 962-966.

* cited by examiner

*Primary Examiner* — Sanza McClendon
(74) *Attorney, Agent, or Firm* — McKenna, Long & Aldridge LLP

(57) ABSTRACT

The present invention relates to a novel fluorinated compound, a composition comprising the same, and a method for manufacturing a film by using the same, and more particularly a novel compound having a structure in which one or more fluorine and acrylate-based functional groups are substituted in a silane core, a composition comprising the compound and photoinitiator, and a method for manufacturing a film by using the same. If the composition comprising the compound according to the present invention is used, it is possible to manufacture a film in which a refractive index is low, reflectivity is reduced, and transmissivity is increased.

13 Claims, 1 Drawing Sheet

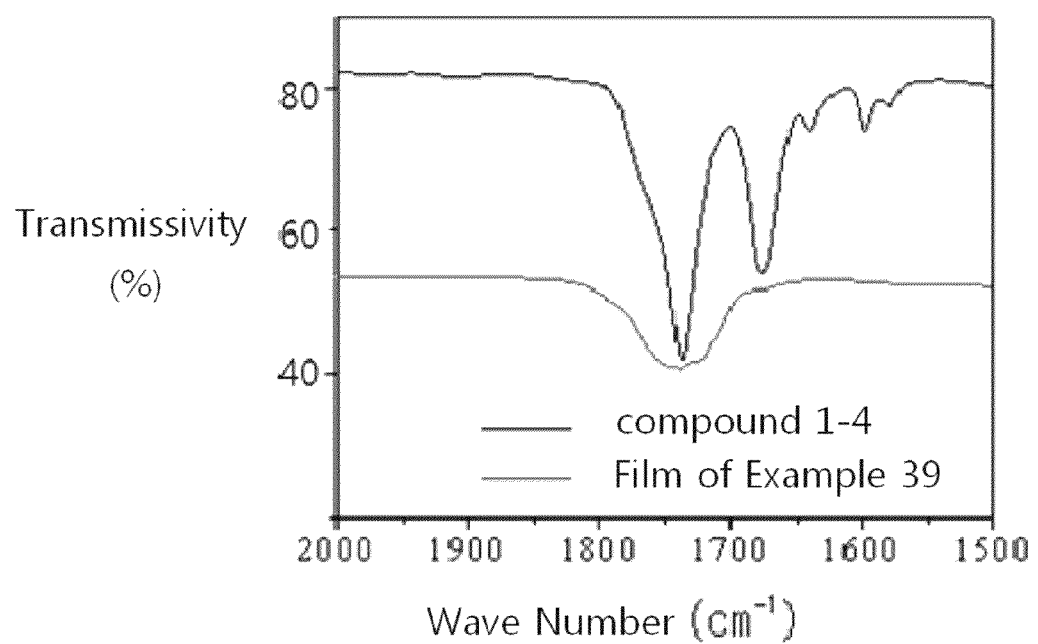

FLUORINATED COMPOUND, A COMPOSITION COMPRISING THE SAME, AND A PRODUCTION METHOD FOR A FILM USING THE SAME

This application is a national stage application of PCT/KR2011/000696, filed Feb. 1, 2011, which claims priority from Korean Patent Application No. 10-2010-0010653, filed on Feb. 4, 2010, in the KIPO, the disclosures of which are incorporated herein by reference in their entireties.

TECHNICAL FIELD

The present invention relates to a novel fluorinated compound, a composition comprising the same, and a method for manufacturing a film by using the same.

BACKGROUND ART

In accordance with the development of display and information communication technologies such as internet and e-commerce currently propagated, a need for optical communication, optical information processing and high-resolution displays having a large capacity is required. In particular, in display diodes, manufacturing of an AR (anti-reflection) layer preventing a reflection phenomenon occurring by reflection of an external light source is one of the important technologies, and the AR layer dissipates and interferes rays reflecting from an interface by using a difference between refractive indexes of two layers, and is generally formed of a multilayered structure of a low refractive material and a high refractive material or a gradient single layer structure in which a refractive index distribution is asymmetric. Since the antireflection is more effective as the refractive index of the low refractive layer is decreased, a technology for controlling the refractive index of the low refractive layer is very important.

As the low refractive optical material, a fluorine-based monomer and a fluorine-based polymer manufactured therefrom has attracted large attention as a material for controlling a refractive index because they have a low refractive index and a low absorption loss at a wavelength of visible ray and IR regions.

For example, U.S. Pat. Nos. 4,985,473, 6,306,563 and 6,323,361 disclose a composition comprising a perfluorinated acrylate derivative having an epoxy group or an unsaturated group and an optical diode manufactured by using the same. A thin film having low loss and low anisotropic properties may be manufactured from the composition, but since the manufactured thin film has low polarity, an attachment property to a substrate is low, and compatibility to a dye added for controlling a refractive index and improving properties is low, such that transmissivity is low and there is a difficulty in improving a function thereof.

In addition, it is difficult to manufacture a monomer having a polyvalent functional group. As the functional group interacting with the substrate, compounds comprising carbonate (—O—C(=O)—O—) having high polarity or a carbamate (—NH—C(=O)—O—) functional group in a molecule thereof are known (Korean Patent Laid-Open Publication No. 2003-0097532), but since the compounds have a relatively high monomer refractive index of 1.4 or more, it is difficult to use the compounds as a low refractive thin film.

DISCLOSURE

Technical Problem

The present invention has been made in an effort to provide a compound that has a low refractive index and can perform light polymerization.

Further, the present invention has been made in an effort to provide a composition comprising the compound and a low refractive film using the same.

Technical Solution

An exemplary embodiment of the present invention provides a compound represented by the following Formula 1 and a method for manufacturing the same.

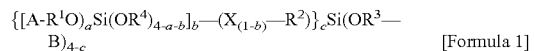
[Formula 1]

wherein
$R^1$ and $R^3$ may be the same as or different from each other, and are each independently a linear or branched alkylene group in which fluorine is substituted and the number of carbon atoms is 1 to 20, and the number of substituted fluorine is 1 to 36;

$R^2$ is an alkylene group having the number of carbon atoms of 1 to 20, or a linear or branched alkylene group in which fluorine is substituted and the number of carbon atoms is 1 to 20, and the number of substituted fluorine is 1 to 36;

$R^4$s may be the same as or different from each other, and are each independently a linear or branched alkyl group in which fluorine is substituted and the number of carbon atoms is 1 to 20, and the number of substituted fluorine is 1 to 36;

A and B may be the same as or different from each other, and are each independently an acrylate-based or methacrylate-based functional group;

X is F or H;

a is an integer in the range of 1 to 3, b is 0 or 1, and c is an integer in the range of 1 to 3.

Another exemplary embodiment of the present invention provides a composition comprising, on the basis of a total weight of a composition i) 0.1 to 99.9 parts by weight of one or more compounds selected from the group consisting of the compounds represented by the Formula 1, and ii) 0.01 to 30 parts by weight of photoinitiator. The composition of the present invention may further comprise iii) 0.1 to 99 parts by weight of one or more selected from the group consisting of a binder, a comonomer having an unsaturated group and a solvent.

Yet another exemplary embodiment of the present invention provides a film manufactured from the composition and a method for manufacturing the same.

Advantageous Effects

According to the exemplary embodiments of the present invention, if the composition comprising the compound according to the exemplary embodiment of the present invention is used, since a refractive index is low, transmissivity, reflectivity, attachment property to a substrate, and compatibility to a dye are excellent, chemical resistance to an organic solvent that is generally used is excellent, it is possible to provide a shaped body and an optical diode having excellent reliability.

DESCRIPTION OF DRAWINGS

FIG. 1 illustrates a light polymerization dynamic of a composition manufactured according to Example 39 of the present invention.

BEST MODE

Hereinafter, the present invention will be described in detail.

The present invention relates to a compound represented by the following Formula 1, in which one or more fluorine and acrylate-based functional groups are substituted in a silane core.

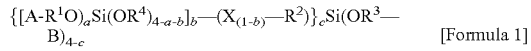

[Formula 1]

wherein $R^1$ and $R^3$ may be the same as or different from each other, and are each independently a linear or branched alkylene group in which fluorine is substituted and the number of carbon atoms is 1 to 20, and the number of substituted fluorine is 1 to 36;

$R^2$ is an alkylene group having the number of carbon atoms of 1 to 20, or a linear or branched alkylene group in which fluorine is substituted and the number of carbon atoms is 1 to 20, and the number of substituted fluorine is 1 to 36;

$R^4$s may be the same as or different from each other, and are each independently a linear or branched alkyl group in which fluorine is substituted and the number of carbon atoms is 1 to 20, and the number of substituted fluorine is 1 to 36;

A and B may be the same as or different from each other, and are each independently an acrylate-based or methacrylate-based functional group;

X is F or H;

a is an integer in the range of 1 to 3, b is 0 or 1, and c is an integer in the range of 1 to 3.

The compound of Formula 1 may be represented by the following Formula 1-a or Formula 1-b.

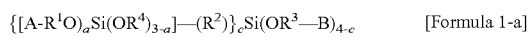

[Formula 1-a]

[Formula 1-b]

wherein, R1 to R4, A, B, X, a and c are the same as the definitions of those of Formula 1.

Detailed examples of the compounds corresponding to the Formula 1 will be shown below, but are not limited thereto.

[Compound 1-1]

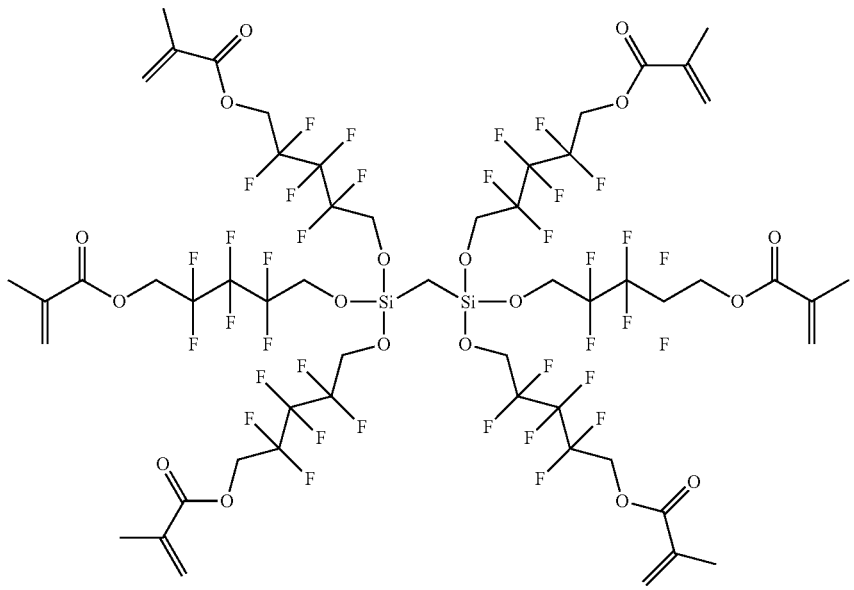

[Compound 1-2]

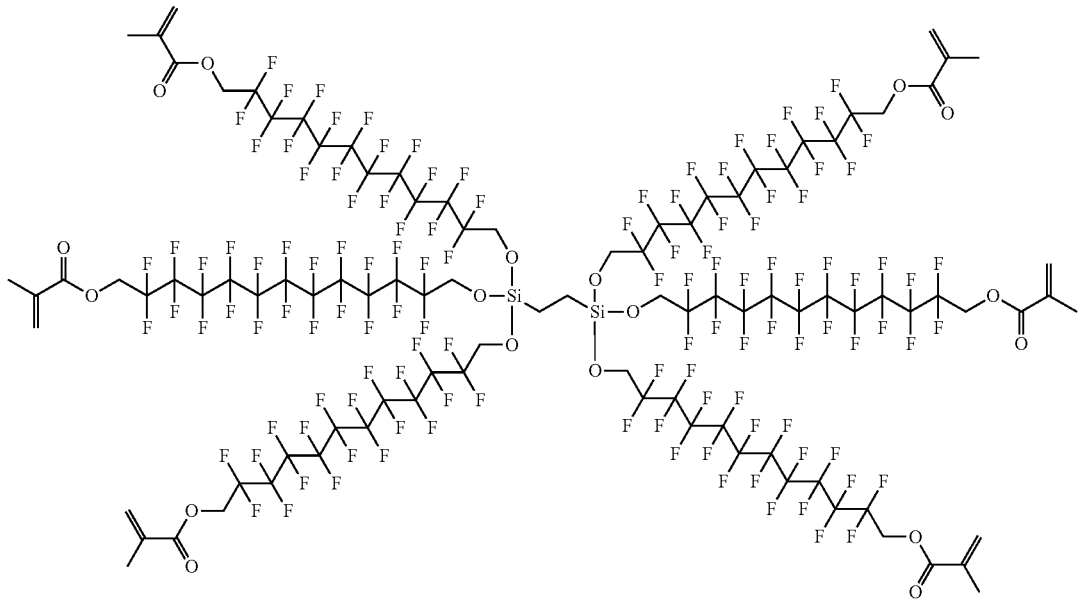

[Compound 1-3]
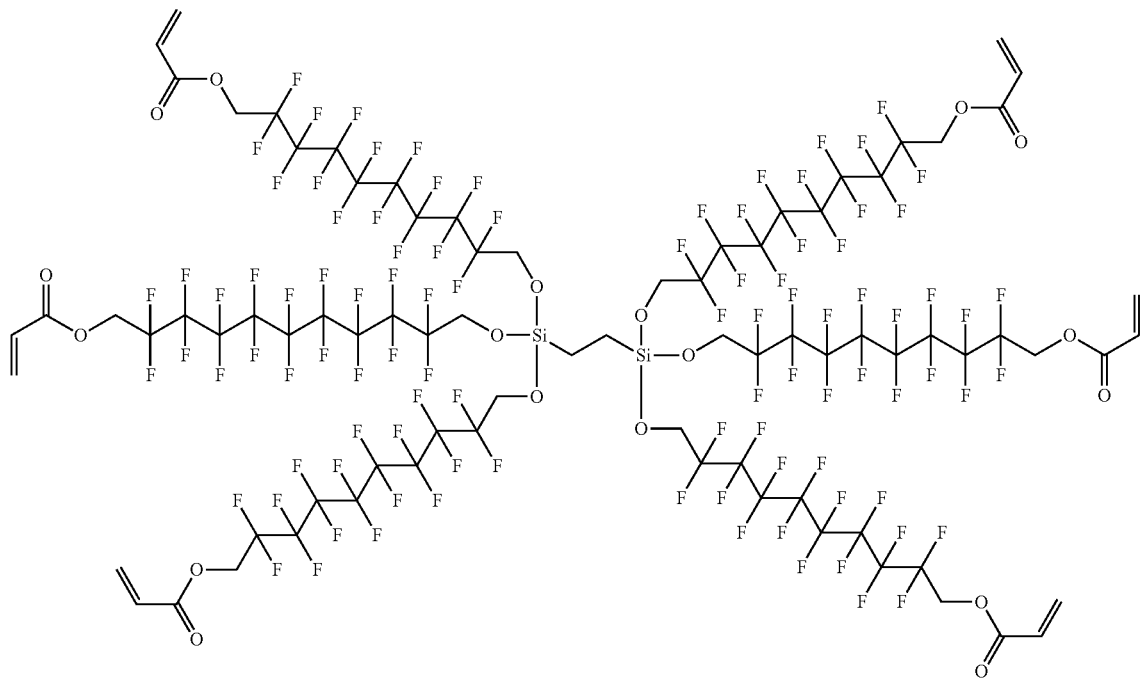
[Compound 1-4]
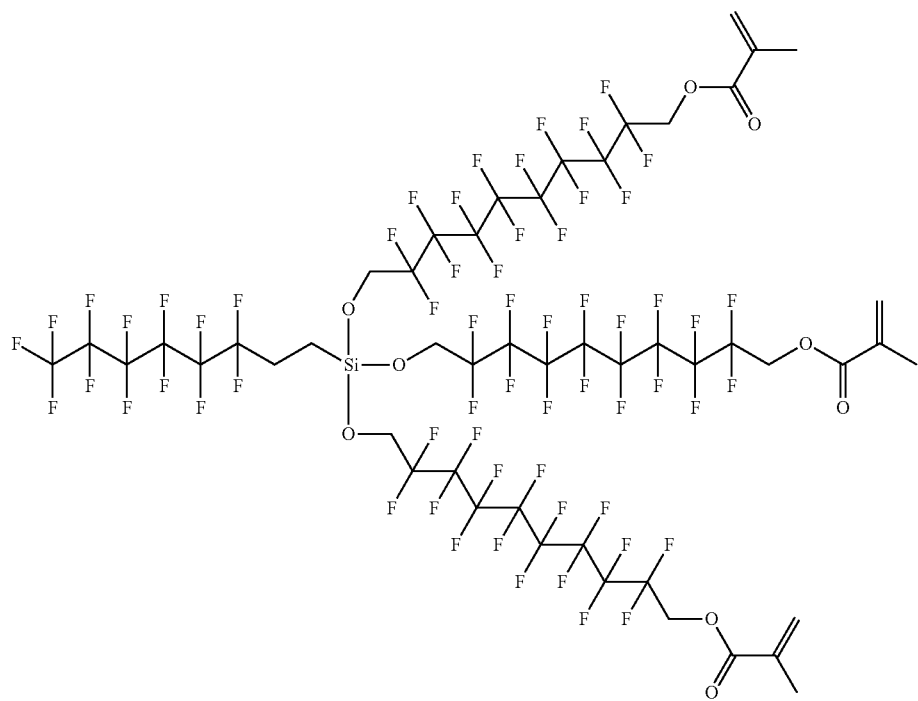

[Compound 1-5]
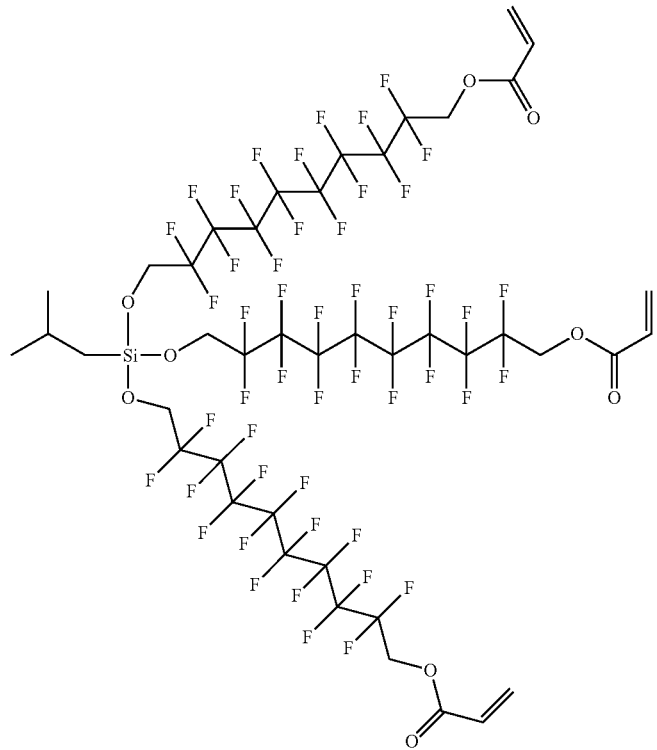
[Compound 1-6]
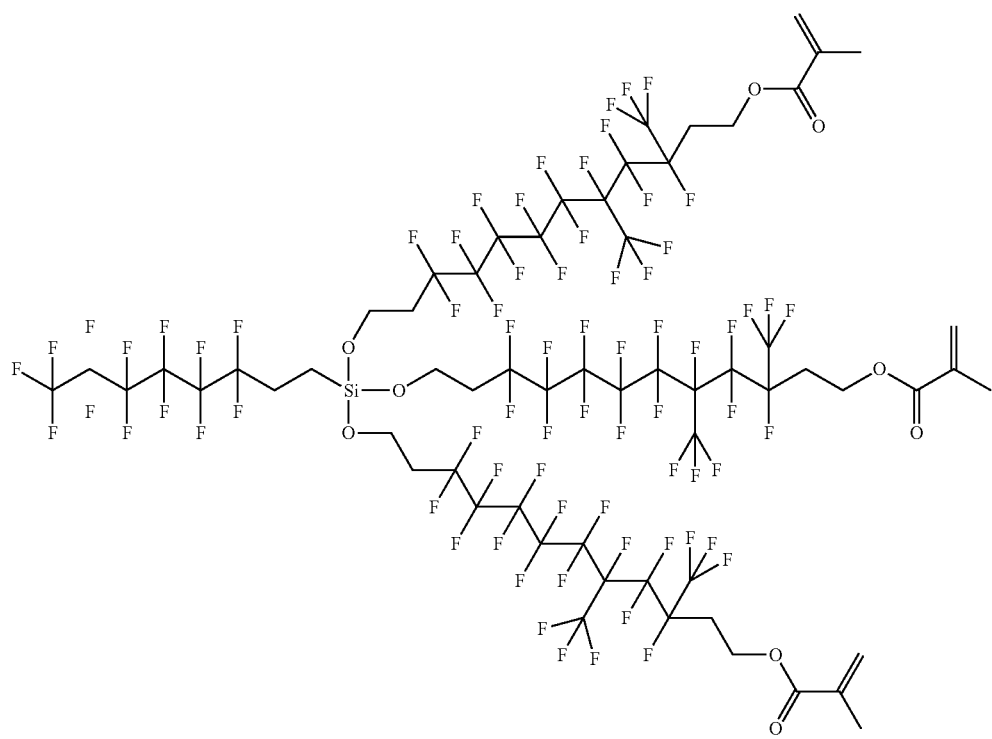

-continued
[Compound 1-7]
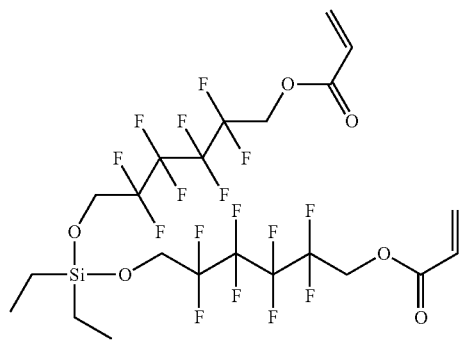
[Compound 1-8]
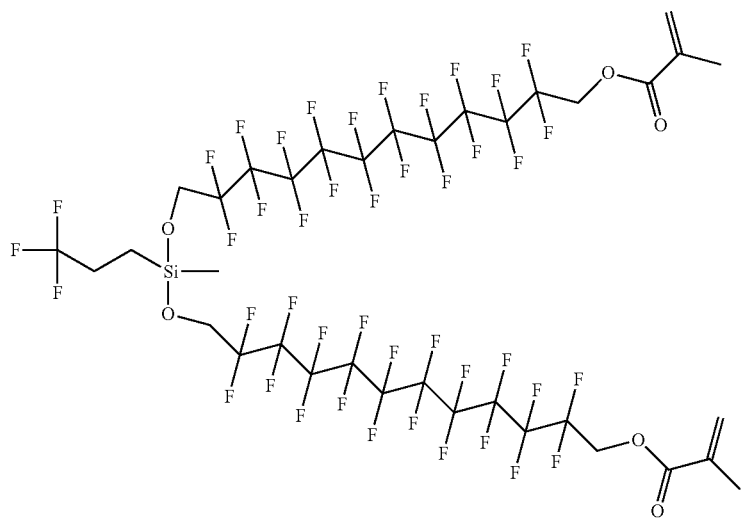
[Compound 1-9]
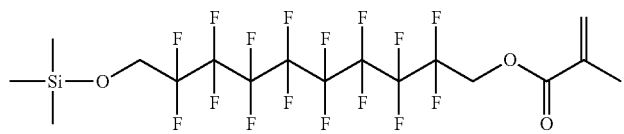
[Compound 1-10]
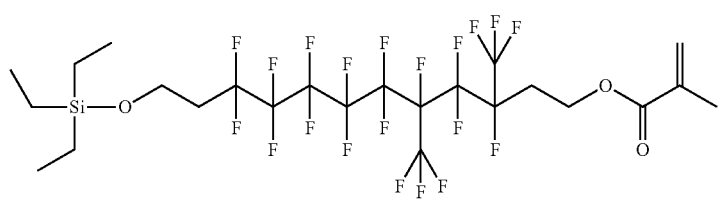

[Compound 1-11]

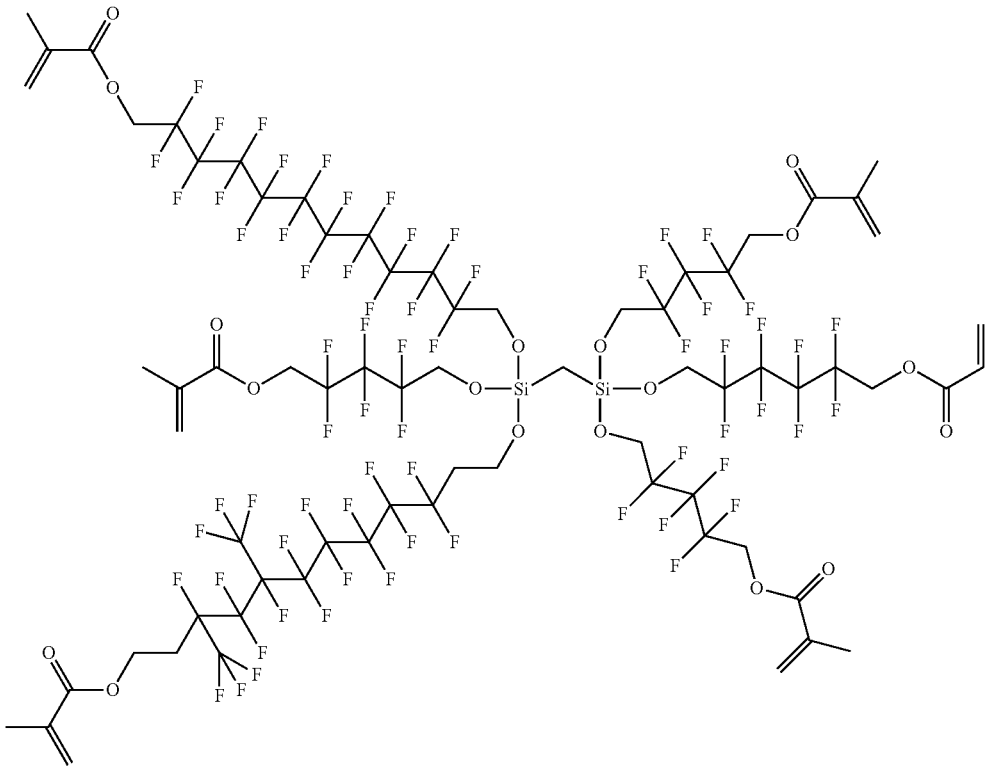

In the compound, light polymerization can be feasible by comprising an acrylate-based functional group, and a refractive index is reduced by increasing the content of fluorine. In addition, an attachment ability after light curing can be improved, reactivity of a fluorinated alkyl chain can be increased, and an attachment property to an interface can be improved by using a material of a silane core that can interact with the substrate.

In addition, the compound has a heat polymerization property.

A method for manufacturing the compound represented by the Formula 1 will be described below, but is not limited thereto.

That is, the compound represented by the Formula 1 is manufactured by using the compound of the following Formula 2, and the compound of the following Formula 3 or one or more compound of aromatic alcohol, and may be manufactured without a solvent or by using one or more solvents selected from MC (dichloromethane, $CH_2Cl_2$), DMF (dimethylformamide), THF (tetrahydrofuran), DMSO (dimethylsulfoxide), EA (Ethyl acetate), IPA (Isopropyl alcohol), and EC(ethylene carbonate) at a temperature of −20 to 110° C., and preferably −10 to 70° C. with agitation for 10 min to 48 hours or more.

$$\{[(Y)_aSi(OR^4)_{4-a-b}]_b—(X_{(1-b)}—R^2)\}_cSi(Z)_{4-c}$$ [Formula 2]

wherein
X is F or H;
Y and Z are each independently a halogen atom,
$R^2$ is an alkylene group having the number of carbon atoms of 1 to 20, or a linear or branched alkylene group in which fluorine is substituted and the number of carbon atoms is 1 to 20, and the number of substituted fluorine is 1 to 36;

$R^4$s may be the same as or different from each other, and are each independently a linear or branched alkyl group in which fluorine is substituted and the number of carbon atoms is 1 to 20, and the number of substituted fluorine is 1 to 36;

a is an integer in the range of 1 to 3, b is 0 or 1, and c is an integer in the range of 1 to 3.

$$R^5—C$$ [Formula 3]

wherein
$R^5$ is a linear or branched alkyl group in which a hydroxyl group and fluorine are substituted and the number of carbon atoms is 1 to 20, and the number of substituted fluorine is 1 to 36;
C is an acrylate-based or methacrylate-based functional group.

Detailed examples of the compounds corresponding to Formula 2 and Formula 3 will be shown below, but are not limited thereto.

[Compound 2-1]

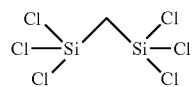

[Compound 2-2]

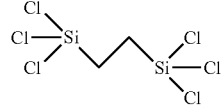

[Compound 2-3], [Compound 2-4], [Compound 2-5], [Compound 2-6], [Compound 2-7], [Compound 2-8], [Compound 2-9], [Compound 2-10], [Compound 2-11]

The compounds 2-1 to 2-11 may be purchased from Sigma Aldrich, Co., Ltd., Gelest Inc., and Merck, Co., Ltd.

[Compound 3-1], [Compound 3-2], [Compound 3-3], [Compound 3-4], [Compound 3-5], [Compound 3-6], [Compound 3-7]

Diol in which fluorine that is a starting material of the compound 3-1 is substituted was purchased from Exfluor Chem., Co., Ltd., and a branched fluoro diol chain of the compound 3-4 was synthesized according to U.S. Pat. No. 5,204,441. In addition, a synthesis method for substituting acrylate or methacrylate was performed referring to the paper [Chem. Mater, 2005, 17(5) 962].

The compound of the Formula 1 according to the exemplary embodiment of the present invention manufactured by using the above method has a very low refractive index of 1.39 or less. In addition, if the composition to which the compound and the photoinitiator are added is exposed to heat or light (UV, visible rays, and IR), a low refractive transparent thin film is manufactured.

It is more preferable that the compound according to the exemplary embodiment of the present invention, as shown in the Formula 1-b, comprises at least two silane groups therein, and if the composition comprising the compound of the Formula 1-b is used, a refractive index is low, since a refractive index is low, transmissivity, reflectivity, attachment property to a substrate, and compatibility to a dye are excellent, and chemical resistance to an organic solvent that is generally used is excellent, it is possible to provide a shaped body and an optical diode having excellent reliability.

In addition, the composition comprising the compound of the Formula 1 according to the exemplary embodiment of the present invention will be described below.

The composition according to the exemplary embodiment of the present invention may comprise, on the basis of a total weight of a composition i) 0.1 to 99.9 parts by weight of one or more compounds selected from the group consisting of the compounds represented by the Formula 1, and ii) 0.01 to 30 parts by weight of photoinitiator, and the composition may further comprise iii) 0.1 to 99 parts by weight of one or more selected from the group consisting of a binder, a comonomer having an unsaturated group and a solvent.

In particular, in the composition according to the exemplary embodiment of the present invention, the compound represented by the Formula 1 may comprise a compound represented by the Formula 1-a; a compound represented by the Formula 1-b; or a mixture of a compound represented by the Formula 1-a and a compound represented by the Formula 1-b.

The photoinitiator includes a radical initiator and an acid generation initiator, and an initiator that is generally used in the art can be used, but the photoinitiator is not particularly limited thereto. Preferably, one or more initiators selected from Cyracure UVI-6990 and Cyracure UVI-6974 products manufactured by Union Carbide, Co., Ltd.; Degacure manufactured by Degusa, Co., Ltd., SP-55, SP-150, and SP-170 products manufactured by AsahiDenka, Co., Ltd.; Irgacure 261, Irgacure 184, Irgacure 819, Irgacure 907, Irgacure 2959, Irgacure 500, Irgacure 127, Irgacure 754, Irgacure 369, Irgacure 651, and Irgacure 2100 products manufactured by Ciba-Geigy, Co., Ltd., Darocure 1173, Darocure 4265, Darocure 4265, Darocure 1664, Darocure MBF, and Darocure TPO products manufactured by Fluca, Co., Ltd. may be used.

The content of the photoinitiator, on the basis of the total weight of the composition, is 0.01 to 30 parts by weight, and preferably 0.01 to 20 parts by weight. If the content is less than 0.01 parts by weight, there may be a problem in that a reaction may be slow or a molecular weight may be reduced, and if the content is more than 30 parts by weight, there may be a problem in that a polymerization speed may become slow or it is difficult to perform polymerization, such that it is preferable to maintain the content in the above range.

As the above binder, a binder that is generally used in the art may be used, but is not particularly limited. Preferably, one or more selected from a fluorine resin, PES (poly ether sulfone), polystyrene, polyethyleneglycol, polycarbonate, polyimide, polyester, polysiloxane, PMMA (polymethylmethacrylate), and PDMS (polydimethylsiloxane) may be used.

The content of the binder, on the basis of the total weight of the composition, is 0.1 to 99 parts by weight, and preferably 30 to 90 parts by weight. If the binder is used in the above range, there is an advantage in that a thin film is uniform.

As the comonomer comprising the unsaturated group, one or more selected from the group consisting of a unsaturated compound widely known in the art, an acrylate or methacrylate-based compound, a fluorinated alkyl chain compound in which acrylate or methacrylate is substituted, a monomer synthesized by a known method (ref. E. kim. S. Cho. D. Yeu, S. Shin. Chem. Mater. 2005, 17, 962 or Korean Patent Laid-Open Publication No. 2003-0097532), a monomer manufactured according to a method known to U.S. Pat. Nos. 4,985, 473, 6,306,563 and 6,323,361, and a composition thereof may be used.

The unsaturated group means a vinyl group, an acetylene group, and an epoxy group.

The content of the comonomer comprising the unsaturated group, on the basis of the total weight of the composition, is 0.1 to 99 parts by weight, and preferably 20 to 95 parts by weight. If the comonomer comprising the unsaturated group is used in the above content range, there are advantages in that a refractive index can be controlled and a thin film becomes uniform.

An organic solvent well known in the art may be further used in the composition. As the solvent, one or more selected from the group consisting of tetrahydrofurane, chloroform, tetrachloromethane and tetrachloroethane may be used, or one or more selected from the group consisting of trifluoroethanol, methanol, ethanol, isopropanol, n-butanol, methylisocarbinol, acetone, 2-butanone, ethyl amyl ketone, diacetonealcohols, isopropanone, cyclohexanone, N,N-dimethylformaide, N,N-dimethylacetoamide, diethyl ether, diisopropyl ether, 1,4-dioxane, 3,4-dihydro-2H-pyran, 2-methoxy ethanol, 2-ethoxy ethanol, 2-butoxy ethanol, ethylene glycol dimethyl ether, methyl acetate, ethyl acetate, isobutyl acetate, amyl acetate, ethyl lactate, ethylene carbonate; aromatic hydrocarbons such as benzene, toluene, xylene, hexane, peptane, iso-octane, and cyclohexane, methylene chloride, 1,2-dichloroethane, dichloropropane, chlorobenzene, dimethylsulfoxide, and N-methyl-2-pyrrolidone may be used.

The content of the solvent, on the basis of the total weight of the composition, is 0.1 to 99 parts by weight, and preferably 10 to 95 parts by weight. If the solvent is used in the above range, there is an advantage in that a thickness of a thin film can be controlled.

A refractive index of the composition comprising the compound of the Formula 1 according to the exemplary embodiment of the present invention is in the range of 1.38 to 1.44.

In addition, the present invention provides a low refractive film that is manufactured by drying the composition according to the exemplary embodiment of the present invention at −20 to 110° C., forming a film, and irradiating light thereto and a method for manufacturing the same.

According to the exemplary embodiment of the present invention, a polymer thin film or polymer shaped body may be manufactured by adding the composition according to the exemplary embodiment of the present invention into a mold, or coating the composition on a support such as, for example, a glass substrate, and a resin film, drying the composition at normal temperature to 80° C., and irradiating light such as UV, visible rays, electronic beams, X-rays, and gamma rays.

In this case, the coating may be methods such as roll coating, spin coating, bar coating, spray coating, and deep coating, and the thickness of the thin film may be generally in the range of 0.01 μm to 3 mm.

Since the manufactured polymer thin film and shaped body has a low refractive index, excellent compatibility to a dye and attachment property to a substrate, and particularly excellent chemical resistance to an organic solvent that is generally used, it is possible to provide an antireflection film and an optical diode having excellent reliability.

MODE FOR INVENTION

The present invention will be described in detail through the following Examples. However, the Examples are set forth to illustrate but are not to be construed to limit the scope of the present invention.

EXAMPLE

Measurement Method of Physical Properties

1) Refractive index; The refractive index of the manufactured compound or composition was measured by using SPA-400 manufactured by SAIRON Tech, Co., Ltd. under the light source having the wavelength of 650 mm.

2) Transmissivity; The transmissivity was measured by using the film having the coating thickness of 100 nm on the PET film from AvaSec-2048 manufactured by Avantes, Co., Ltd.

3) Light polymerization characteristic; A change of intensity of the C=C vibration wave number of the unsaturated group was measured by using the infrared spectroscopy, and Tensor 37 manufactured by Bruker, Co., Ltd. was used.

Preparation Example 1

Preparation of the Compound 3-1

0.047 mol of 1H,1H,5H,5H-perfluoro-1,5-pentanediol and 100 ml of anhydrous THF were mixed with each other in 250 ml of round bottom flask. 0.047 mol of triethylamine was added thereto under the nitrogen atmosphere. After the agitation for 1 hour, 0.047 mol of methacryloyl chloride was slowly added thereto. The reaction mixture was agitated for 3 days at room temperature. After the reaction was finished, the precipitate was filtered through a filter, 100 ml of dichloromethane was added thereto, and they were extracted by using the aqueous solution in which sodium bicarbonate was dissolved.

The solvent was removed from the solution filtered through the extraction process, and the solution was purified through the silica gel column chromatography using the developing solvent (1:2) of petroleum ether and tetrahydrofuran.

The final resulting material showed the yield of 55%.

Preparation Example 2

Preparation of the Compound 3-4

Preparation Example 2 was performed in the same manner as Preparation Example 1, except that chloride and 2,2,3,3,4,4,5,5-octafluoro-1,6-hexanediol were reacted with each other, thereby manufacturing the compound 3-4, and the yield of the final resulting material was 65%.

Preparation Example 3

Preparation of the Compound 3-5

Preparation Example 3 was performed in the same manner as Preparation Example 1, except that acryloyl chloride and 2,2,3,3,4,4,5,5,6,6,7,7,8,8,9,9-hexadecafluoro-1,10-decanediol were reacted with each other, thereby manufacturing the compound 3-5, and the yield of the final resulting material was 62%.

Example 1

Preparation of the Compound 1-4

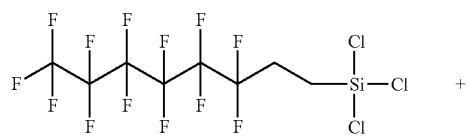

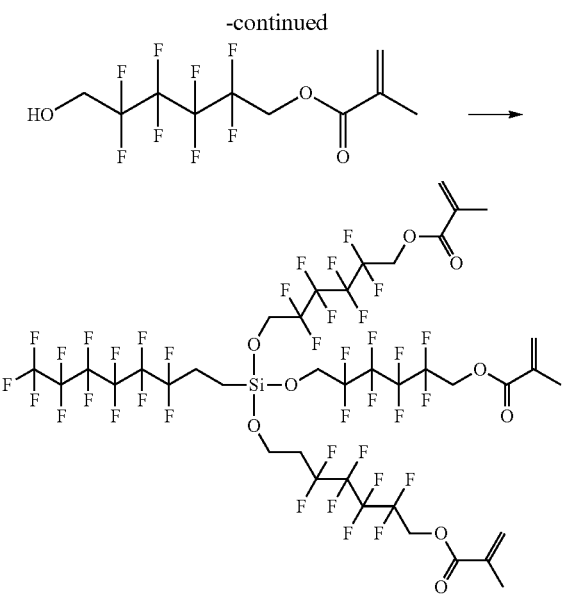

0.5 mol of silane chloride of Formula 2-3, and 1.5 mol of fluorinated alkyl methacrylate of Formula 3-7 were put into the round bottom flask of 50 ml under the nitrogen atmosphere by using the material obtained by Preparation Example 1, and agitated for 7 hours while the organic solvent was not added thereto. The reaction temperature in this case was continuously maintained at 0° C. The obtained material was purified through the silica gel column chromatography using the developing solvent (1:2) of petroleum ether and dichloromethane.

The final resulting material showed the yield of 90%.

Examples 2 to 12

Preparation of the Compounds 1-1 to 1-11

The material was synthesized according to the method of Example 1, and the synthesized material and reaction condition are described in the following Table 1. The yield, $^1$H NMR and $^{19}$F NMR of the synthesized final resulting material are described in the following Table 1.

TABLE 1

| | Product compound | Starting material Formula 2 | Starting material Formula 3 | Reaction condition Mole number/time/ temperature/solvent (mL) | Yield (%) | $^1$H NMR (400 MHz, CDCl$_3$), δ | $^{19}$F NMR (400 MHz, CDCl$_3$), δ |
|---|---|---|---|---|---|---|---|
| Example 2 | 1-1 | 2-1 | 3-1 | 2-1: 0.5 mol, 3-1: 3.0 mol/ 7 hour/0° C. | 85 | 0.1/2.2/ 3.5~4.1/ 5.6/15.9 | −120/−123/ −127 |
| Example 3 | 1-2 | 2-2 | 3-3 | 2-2: 0.5 mol, 3-3: 3.0 mol/ 7 hour/0° C./CHCl$_3$(40) | 55 | 0.7/2.3/ 3.4~4.2/ 5.7/5.9 | −120/−123/ −124/−127 |
| Example 4 | 1-3 | 2-2 | 3-5 | 2-2: 0.5 mol, 3-5: 3.0 mol/ 7 hour/0° C./THF(50) | 78 | 0.7/ 3.4~4.2/ 5.7/5.9/ 6.2 | −120/−123/ −124/−127 |

TABLE 1-continued

| | Product compound | Starting material Formula 2 | Formula 3 | Reaction condition Mole number/time/ temperature/solvent (mL) | Yield (%) | $^1$H NMR (400 MHz, CDCl$_3$), δ | $^{19}$F NMR (400 MHz, CDCl$_3$), δ |
|---|---|---|---|---|---|---|---|
| Example 5 | 1-4 | 2-3 | 3-3 | 2-3: 0.5 mol, 3-3: 1.5 mol/ 7 hour/0° C. | 90 | 1.9/2.5/ 3.5~4.7/ 5.8/6.7 | −81/−121/ −123/−126 |
| Example 6 | 1-5 | 2-5 | 3-5 | 2-5: 0.5 mol, 3-5: 1.5 mol/ 7 hour/0° C./THF(50) | 82 | 0.6/1.0/ 1.9/ 3.4~4.2/ 5.7/5.9/ 6.2 | −120/−123/ −124/−127 |
| Example 7 | 1-6 | 2-3 | 3-6 | 2-3: 0.5 mol, 3-6: 1.5 mol/ 7 hour/0° C. | 86 | 0.6/ 1.6~1.7/ 1.9/2.0/ 2.3/ 3.4~4.5/ 5.7/5.9 | −81/−121/ −123/−124/ −126 |
| Example 8 | 1-7 | 2-7 | 3-4 | 2-7: 0.5 mol, 3-4: 1.0 mol/ 7 hour/0° C. | 92 | 1.9/2.5/ 3.5~4.7/ 5.8/6.7 | −120/−122/ −124/−128 |
| Example 9 | 1-8 | 2-6 | 3-3 | 2-6: 0.5 mol, 3-3: 1.0 mol/ 7 hour/0° C. | 84 | 1.3/1.9/ 3.4~4.3/ 5.7/5.9/ 6.2 | −76/−122/ −124/−128 |
| Example 10 | 1-9 | 2-12 | 3-2 | 2-12: 0.5 mol, 3-2: 0.5 mol/ 7 hour/0° C. | 76 | 0.1/2.3/ 4.3~4.5/ 5.7/5.9 | −121/−123/ −124/−126 |
| Example 11 | 1-10 | 2-8 or 2-11 | 3-6 | 2-8 or 2-11: 0.5 mol, 3-6: 0.5 mol/ 7 hour/0° C. | 82 | 1.0/1/6/ 1.7~1.9/ 2.3/ 3.5~4.4/ 5.7/5.9 | −81/−120/ −122/−124/ −126 |
| Example 12 | 1-11 | 2-1 | 3-1, 3-3, 3-4, 3-6 | 2-1: 0.5 mol, 3-1: 1.5 mol, 3-3: 0.5 mol, 3-4: 0.5 mol, 3-6: 0.5 mol/ 7 hour/0° C. | 53 | 0.1/1.7/ 1.9/2.3/ 3.7~4.7/ 5.7/5.8/ 5.9 | −81/−120/ −121/−122/ −123/−124/ −126 |

Examples 13 to 27

Preparation of the Low Refractive Composition

The composition was manufactured by using the material manufactured through Example, the component and the solvent shown in the following Table 2, and the manufacturing method. The refractive index of the manufactured composition was measured, and is described in the following Table 2.

TABLE 2

| composition | Polymerizable material (dg) | Initiator (dg) | Transparent polymer (dg) | Known acrylate material (dg) | Solvent (mL) | Refractive index |
|---|---|---|---|---|---|---|
| Example 13 | Compound 1-1 (3) | Igacure 184 (5) + Darocure 1664 (5) | PDMS (70) | Formula 4 (40) | 2,2,2-trifluoroethanol(10) + chloroform (25) | 1.405 |
| Example 14 | Compound 1-2 (15) | Igacure 2959 (2) | PDMS (45) | — | 2,2,2-trifluoroethanol(10) + IPA (38) | 1.40 |
| Example 15 | Compound 1-3 (5) | Darocure 1173 (2) | — | Formula 4 (40) | 2,2,2-trifluoroethanol(10) + chloroform (33) | 1.38 |
| Example 16 | Compound 1-4 (1) | Darocure 1173 (5) | — | Formula 4 (50) + Formula 5 (10) | 2,2,2-trifluoroethanol(10) + methylene chloride (34) | 1.44 |
| Example 17 | Compound 1-5 (55) | SP-150 (2) + Igacure 784 (3) | PDMS (5) | — | THF (35) | 1.42 |
| Example 18 | Compound 1-6 (70) | Igacure 261 (10) | PMMA (2) + PDMS (2) | Formula 4 (2) | IPA (14) | 1.41 |
| Example 19 | Compound 1-7 (10) | Darocure 1173 (2) | — | Formula 4 (60) + Formula 5 (10) | methylene chloride (18) | 1.43 |

TABLE 2-continued

| composition | Polymerizable material (dg) | Initiator (dg) | Transparent polymer (dg) | Known acrylate material (dg) | Solvent (mL) | Refractive index |
|---|---|---|---|---|---|---|
| Example 20 | Compound 1-8 (2) | Darocure 1173 (5) | — | Formula 6 (2) | IPA (44) + EC (44) | 1.42 |
| Example 21 | Compound 1-9 (2) | Igacure 261 (10) | PMMA (10) + PDMS (10) | — | chloroform (68) | 1.42 |
| Example 22 | Compound 1-10 (10) | Darocure 1173 (5) + SP-170 (5) | PMMA (30) | Formula 6 (5) | chloroform (45) | 1.41 |
| Example 23 | Compound 1-11 (15) | Igacure 819 (0.1) | PDMS (25) | Formula 5 (5) | methylene chloride (54.9) | 1.40 |
| Example 24 | Compound 1-4 (95) | Darocure 1173 (5) | — | — | — | 1.39 |
| Example 25 | Compound 1-4 (5) compound 1-11 (5) | Igacure 819 (1) | PMMA (30) | — | EA (59) | 1.41 |
| Example 26 | Compound 1-1 (5) Compound 1-9 (5) | SP-150 (2) + Igacure 784 (3) | — | Formula 7 (5) + Formula 5 (10) | methylene chloride (70) | 1.42 |
| Example 27 | Compound 1-2 (5) Compound 1-7 (5) | Darocure 1173 (2) | PDMS (2) | — | 2,2,2-trifluoroethanol(10) + THF (42) | 1.383 |

The compounds of Formula 4 to Formula 7 described in Table 2 are shown below.

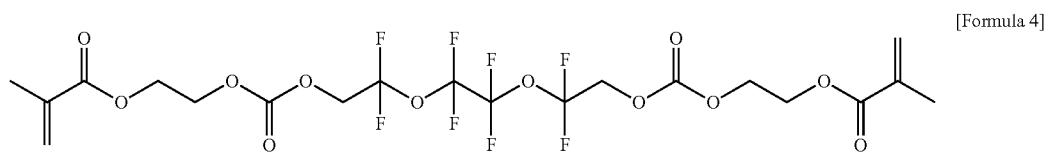

[Formula 4]

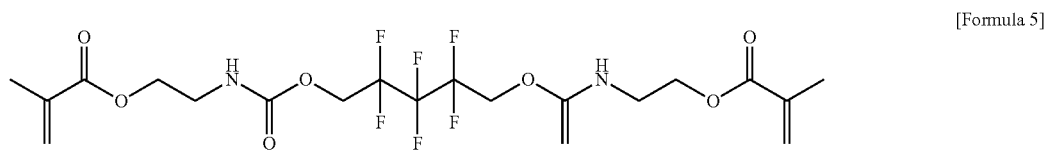

[Formula 5]

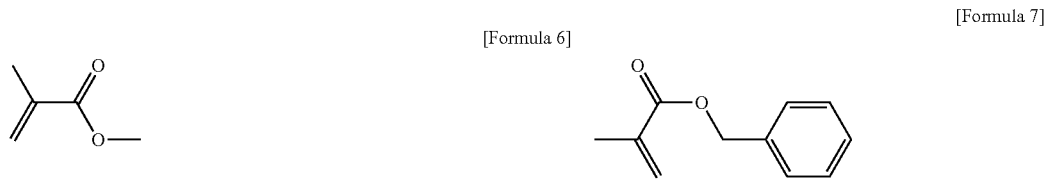

[Formula 6]

[Formula 7]

Example 28

Method for Manufacturing the Low Reflective Film

The low reflective film of 100 nm was manufactured by coating the composition manufactured in Example 16 on the PET film, performing the spin coating at 1,500 rpm for 30 sec, drying the composition at 60° C. in the oven for 2 min, and irradiating UV of the high pressure mercury lamp for 5 min.

The transmissivity of the manufactured film was 96%, and the reflectivity was 4%.

Examples 29 to 42

The low reflective film of 50 nm to 10 μm was manufactured by coating the compositions manufactured in Examples 13 to 27 on glass, silicon wafer or PET substrate, performing the spin coating at 200 to 2,000 rpm, drying the composition at 60 to 90° C. in the oven for 60 to 120 min, and irradiating UV, visible rays or IR of the high pressure mercury lamp for 3 to 180 min, similarly to Example 28. The measurement results are shown in the following Table 3.

The transmissivity of the manufactured film was 90 to 99%, the reflectivity was 1 to 10%, and the PET film was used as the substrate when the transmissivity was measured.

TABLE 3

| | Composition | Reaction condition coating speed (rpm)/coating time (sec)/drying temperature (° C.)/drying time (min)/light source/light irradiation time (min) | Transmissivity (%) | Reflectivity (%) | Thickness of the film (nm) |
|---|---|---|---|---|---|
| Example 29 | Example 13 | 1800/40/60/8/UV/3 | 95 | 5 | 130 |
| Example 30 | Example 14 | 1500/30/60/2/UV/5 | 96 | 6 | 120 |
| Example 31 | Example 15 | 1500/30/60/2/UV/5 | 94 | 7 | 110 |
| Example 32 | Example 17 | 1800/30/60/2/visible ray (Xenon lamp)/20 | 92 | 5 | 120 |
| Example 33 | Example 18 | 1800/40/60/2/UV/5 | 95 | 5 | 110 |
| Example 34 | Example 19 | 1500/30/40/5/UV/15 | 96 | 6 | 105 |
| Example 35 | Example 20 | 1500/30/60/2/UV/5 | 94 | 7 | 120 |
| Example 36 | Example 21 | 1500/30/60/2/UV/5 | 93 | 6 | 110 |
| Example 37 | Example 22 | 1800/40/60/2/UV/5 | 93 | 5 | 120 |
| Example 38 | Example 23 | 1800/40/60/2/UV/5 | 95 | 6 | 130 |
| Example 39 | Example 24 | 1500/30/60/2/491 nm laser/10 | 96 | 5 | 100 |
| Example 40 | Example 25 | 1800/40/70/3/UV/5 | 94 | 5 | 110 |
| Example 41 | Example 26 | 1500/30/50/15/UV/5 | 91 | 7 | 120 |
| Example 42 | Example 27 | 1500/30/60/2/UV/5 | 92 | 5 | 100 |

As described in Table 3, if the film is manufactured by using the composition according to the exemplary embodiment of the present invention, it can be seen that the low reflective film having the high transmissivity and the low reflectivity can be manufactured.

In addition, the following FIG. 1 illustrates IR spectroscopy spectrum manufactured according to Example 39, and it can be seen that the peak of 1,640 cm$^{-1}$ position corresponding to the vibration of the C=C double bond of the unsaturated group shown in the monomer disappears after the film is manufactured due to light irradiation.

The invention claimed is:

1. A compound represented by the following Formula 1:

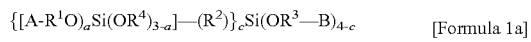
[Formula 1a]

wherein

R$^1$ and R$^3$ may be the same as or different from each other, and are each independently a linear or branched alkylene group in which fluorine is substituted and the number of carbon atoms is 1 to 20, and the number of substituted fluorine is 1 to 36;

R$^2$ is an alkylene group which the number of carbon atoms is 1 to 20, or a linear or branched alkylene group in which fluorine is substituted and the number of carbon atoms is 1 to 20, and the number of substituted fluorine is 1 to 36;

R$^4$s may be the same as or different from each other, and are each independently a linear or branched alkyl group in which fluorine is substituted and the number of carbon atoms is 1 to 20, and the number of substituted fluorine is 1 to 36;

A and B may be the same as or different from each other, and are each independently an acrylate or methacrylate functional group;

a is an integer in the range of 1 to 3, b is 0 or 1, and c is an integer in the range of 1 to 3.

2. The compound according to claim 1, wherein the compound is any one of the following compounds:

[Compound 1-1]
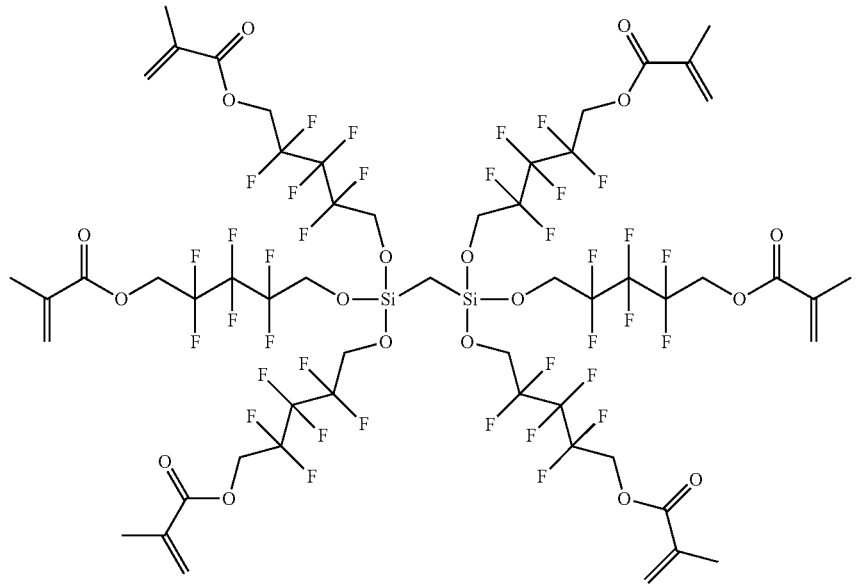
[Compound 1-2]
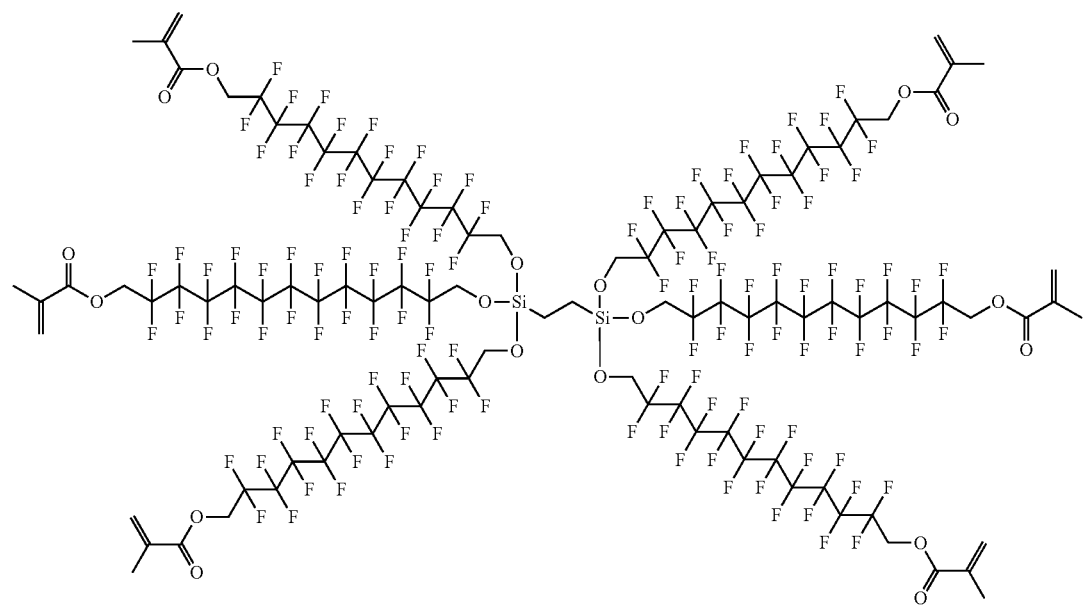

[Compound 1-3]
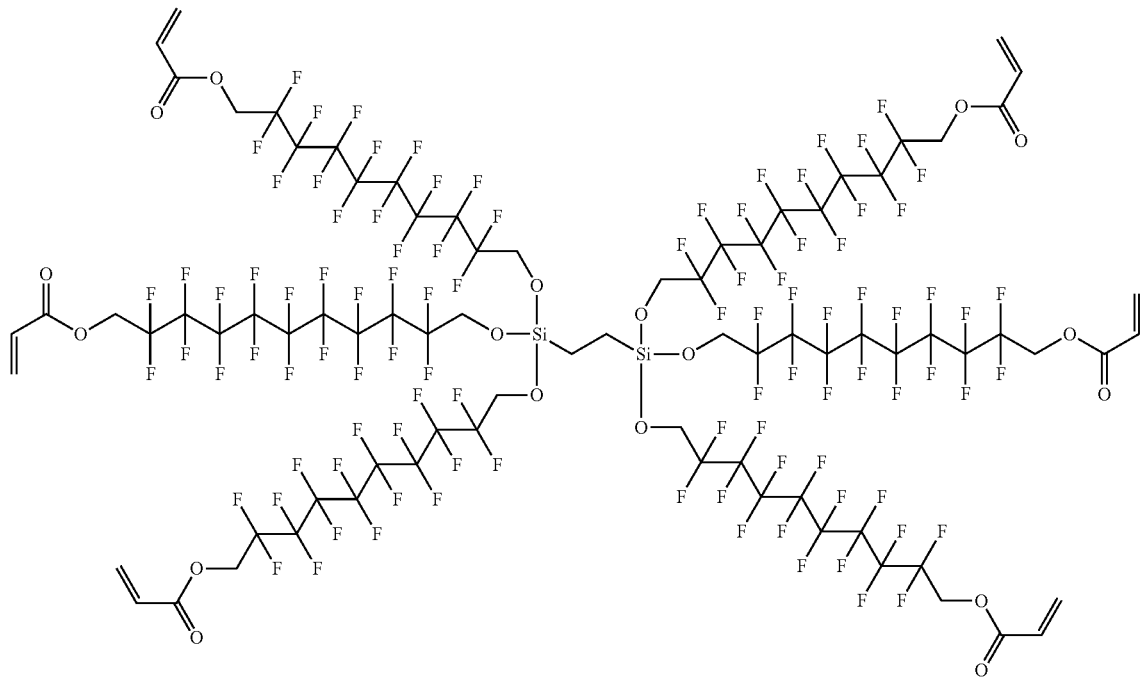
[Compound 1-11]
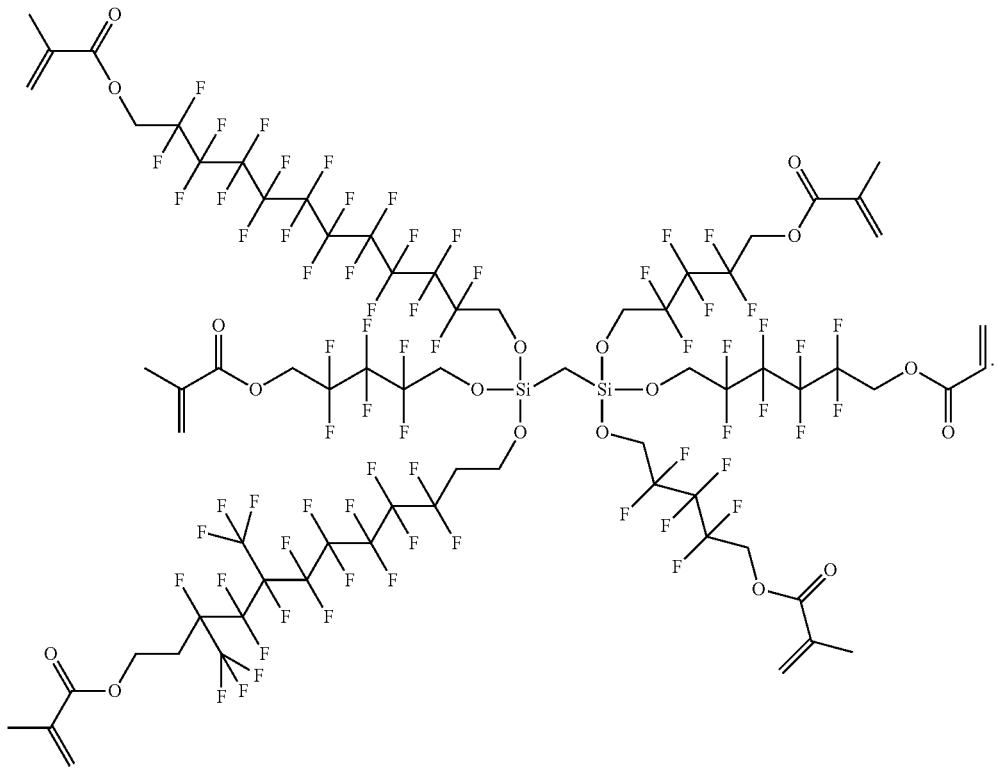

3. A compound represented by any one of the following compounds:
[Compound 1-4]
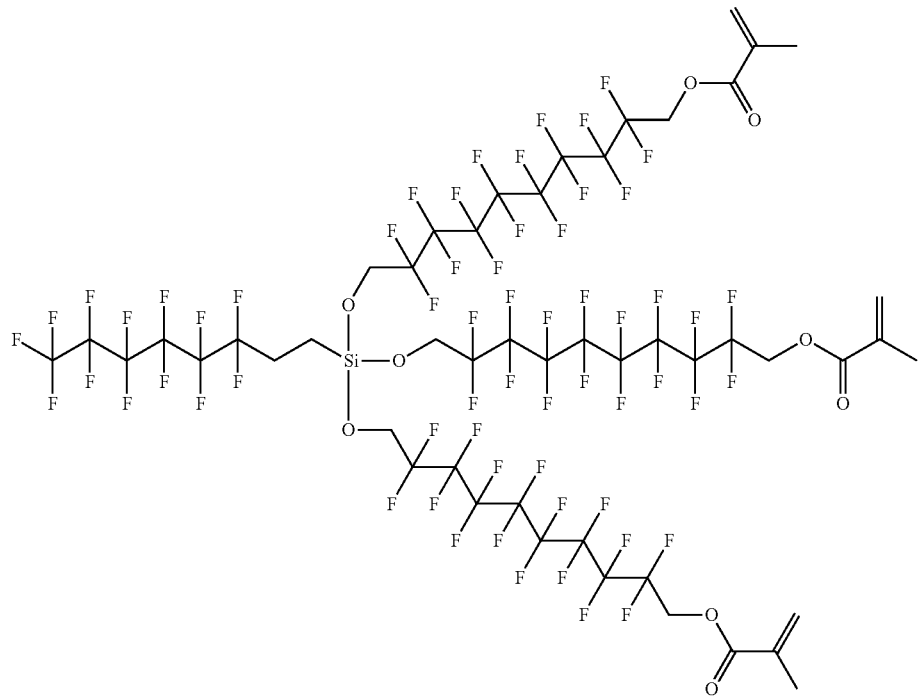
[Compound 1-5]
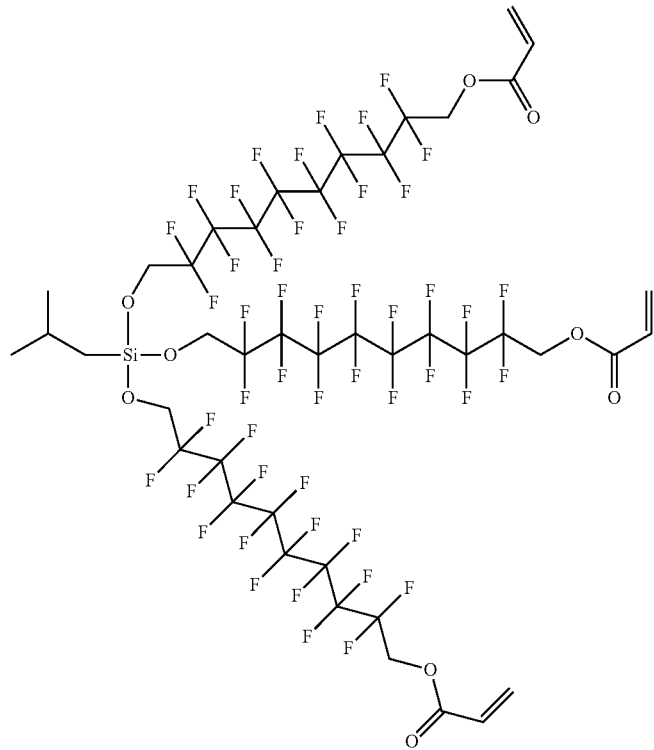

[Compound 1-6]
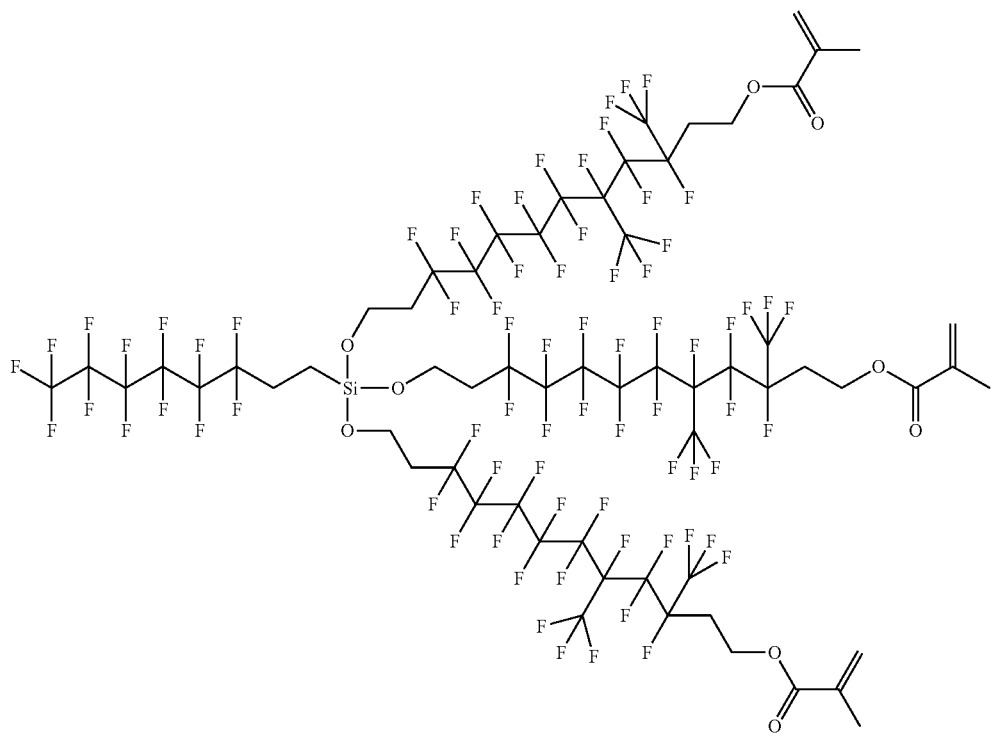
[Compound 1-7]
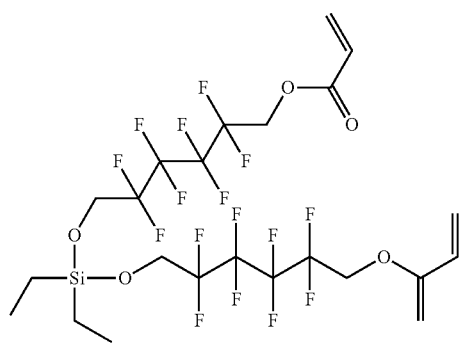
[Compound 1-8]
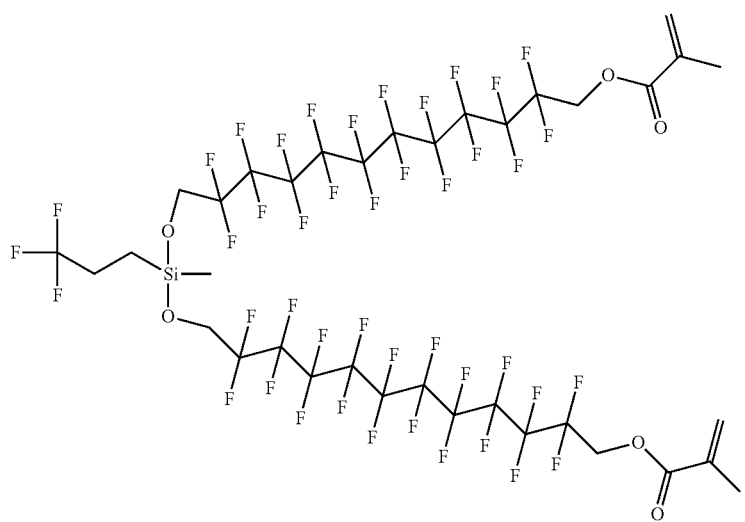

-continued

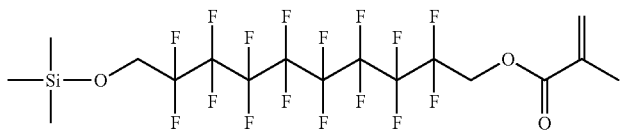
[Compound 1-9]

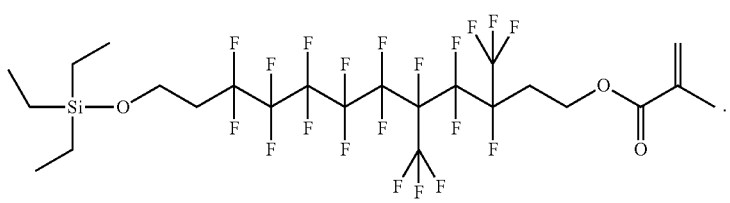
[Compound 1-10]

4. The compound according to claim 1, wherein the compound is manufactured by using a compound of the following Formula 2, and a compound of the following Formula 3 or one or more compounds of aromatic alcohol:

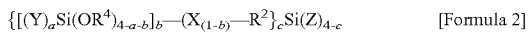
{[(Y)$_a$Si(OR$^4$)$_{4-a-b}$]$_b$—(X$_{(1-b)}$—R$^2$}$_c$Si(Z)$_{4-c}$  [Formula 2]

wherein
X is F or H;
Y and Z are each independently a halogen atom,
R$^2$ is an alkylene group which the number is carbon atoms of 1 to 20, or a linear or branched alkylene group in which fluorine is substituted and the number of carbon atoms is 1 to 20, and the number of substituted fluorine is 1 to 36;
R$^4$s may be the same as or different from each other, and are each independently a linear or branched alkyl group in which fluorine is substituted and the number of carbon atoms is 1 to 20, and the number of substituted fluorine is 1 to 36;
a is an integer in the range of 1 to 3, b is 1, and c is an integer in the range of 1 to 3,

R$^5$—C  [Formula 3]

wherein
R$^5$ is a linear or branched alkyl group in which a hydroxyl group and fluorine are substituted and the number of carbon atoms is 1 to 20, and the number of substituted fluorine is 1 to 36;
C is an acrylate or methacrylate group.

5. A composition comprising, on the basis of a total weight of a composition:
 i) 0.1 to 99.9 parts by weight of one or more compounds selected from the group consisting of the compounds according to claim 1, and
 ii) 0.01 to 30 parts by weight of photoinitiator.

6. The composition according to claim 5, further comprising:
 0.1 to 99.9 parts by weight of the compound represented by the following Formula 1-b:

(X—R$^2$)}$_c$Si(OR$^3$—B)$_{4-c}$  [Formula 1-b]

wherein
R$^3$ is each independently a linear or branched alkylene group in which fluorine is substituted and the number of carbon atoms is 1 to 20, and the number of substituted fluorine is 1 to 36;

R$^2$ is an alkylene group which the number is carbon atoms of 1 to 20, or a linear or branched alkylene group in which fluorine is substituted and the number of carbon atoms is 1 to 20, and the number of substituted fluorine is 1 to 36;
B is each independently an acrylate-based or methacrylate-based functional group;
X is F or H;
c is an integer in the range of 1 to 3.

7. The composition according to claim 5, further comprising:
 iii) 0.1 to 99 parts by weight of one or more selected from the group consisting of a binder, a comonomer having an unsaturated group and a solvent.

8. The composition according to claim 7, wherein the binder is one or more selected from the group consisting of a fluorine resin, poly ether sulfone polystyrene, polyethyleneglycol, polycarbonate, polyimide, polyester, polysiloxane, polymethylmethacrylate and polydimethylsiloxane.

9. The composition according to claim 7, wherein the comonomer comprising the unsaturated group is one or more selected from the group consisting of an acrylate or methacrylate compound; and a fluorinated alkyl chain compound in which acrylate or methacrylate is substituted.

10. The composition according to claim 7, wherein the solvent is one or more selected from the group consisting of tetrahydrofurane, chloroform, tetrachloromethane, tetrachloroethane, methanol, ethanol, isopropanol, n-butanol, methylisocarbinol, acetone, 2-butanone, ethyl amyl ketone, diacetonealcohols, isopropanone, cyclohexanone, N,N-dimethylformaide, N,N-dimethylacetoamide, diethyl ether, diisopropyl ether, 1,4-dioxane, 3,4-dihydro-2H-pyran, 2-methoxy ethanol, 2-ethoxy ethanol, 2-butoxy ethanol, ethylene glycol dimethyl ether, methyl acetate, ethyl acetate, isobutyl acetate, amyl acetate, ethyl lactate, ethylene carbonate, benzene, toluene, xylene, hexane, peptane, iso-octane, cyclohexane, methylene chloride, 1,2-dichloroethane, dichloropropane, chlorobenzene, dimethylsulfoxide and N-methyl-2-pyrrolidone.

11. A shaped body manufactured by using the composition according to claim 5.

12. A method for manufacturing a shaped body by using the composition of claim 5.

13. The method for manufacturing a shaped body according to claim 12, further comprising coating the composition and irradiating light thereon to form a film.

* * * * *